United States Patent
Zhang et al.

(10) Patent No.: US 9,982,128 B2
(45) Date of Patent: *May 29, 2018

(54) FIBERS, WIPES, AND METHODS

(71) Applicant: 3M INNOVATIVE PROPERTIES COMPANY, St. Paul, MN (US)

(72) Inventors: Yifan Zhang, Woodbury, MN (US); Zai-Ming Qiu, Woodbury, MN (US); Liming Song, Woodbury, MN (US); Cordell M. Hardy, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/024,203

(22) PCT Filed: Sep. 17, 2014

(86) PCT No.: PCT/US2014/055981
§ 371 (c)(1),
(2) Date: Mar. 23, 2016

(87) PCT Pub. No.: WO2015/047806
PCT Pub. Date: Apr. 2, 2015

(65) Prior Publication Data
US 2016/0208095 A1  Jul. 21, 2016

Related U.S. Application Data

(60) Provisional application No. 61/884,416, filed on Sep. 30, 2013.

(51) Int. Cl.
| | | |
|---|---|---|
| C08L 67/04 | (2006.01) |
| D04H 1/435 | (2012.01) |
| D01F 1/10 | (2006.01) |
| D01F 6/62 | (2006.01) |
| A01N 25/34 | (2006.01) |
| C08K 5/1515 | (2006.01) |
| C11D 17/04 | (2006.01) |

(52) U.S. Cl.
CPC ............ C08L 67/04 (2013.01); A01N 25/34 (2013.01); C08K 5/1515 (2013.01); C11D 17/049 (2013.01); D01F 1/10 (2013.01); D01F 6/625 (2013.01); D04H 1/435 (2013.01)

(58) Field of Classification Search
CPC ....... A01N 25/34; C08K 5/1515; C08L 67/04; C11D 17/049; D01F 1/10; D01F 6/625; D04H 1/435
See application file for complete search history.

(56) References Cited

U.S. PATENT DOCUMENTS

| | | |
|---|---|---|
| 4,744,365 A | 5/1988 | Kaplan |
| 4,808,467 A | 2/1989 | Suskind |
| 5,475,063 A | 12/1995 | Kaplan |
| 5,498,650 A | 3/1996 | Flexman |
| 5,741,563 A | 4/1998 | Mehta |
| 5,763,538 A | 6/1998 | Hunter |
| 5,834,582 A | 11/1998 | Sinclair |
| 5,883,199 A | 3/1999 | McCarthy |
| 5,952,433 A | 9/1999 | Wang |
| 5,997,568 A | 12/1999 | Liu |
| 6,075,118 A | 6/2000 | Wang |
| 6,093,792 A | 7/2000 | Gross |
| 6,111,060 A | 8/2000 | Gruber |
| 6,113,933 A | 9/2000 | Beerse |
| 6,117,928 A | 9/2000 | Hiltunen |
| 6,143,863 A | 11/2000 | Gruber |
| 6,342,566 B2 | 1/2002 | Burkhardt et al. |
| 6,384,142 B1 | 5/2002 | Brukhardt |
| 7,470,389 B2 | 12/2008 | Berrigan |
| 2,199,456 A1 | 1/2011 | Shimizu |
| 2005/0058673 A1 | 3/2005 | Scholz |
| 2005/0137299 A1 | 6/2005 | Berndt |
| 2006/0142442 A1 | 6/2006 | Scherzer et al. |
| 2008/0038976 A1 | 2/2008 | Berrigan |
| 2009/0110927 A1 | 4/2009 | Mochiduki |
| 2009/0137748 A1 | 5/2009 | Tanaka |
| 2009/0176938 A1 | 7/2009 | Xu |
| 2009/0234094 A1 | 9/2009 | Suzuki |
| 2010/0120991 A1 | 5/2010 | Toyohara |
| 2010/0137526 A1 | 6/2010 | Nakamura |
| 2011/0015310 A1 | 1/2011 | Shimizu et al. |

FOREIGN PATENT DOCUMENTS

| | | |
|---|---|---|
| CN | 101240465 | 8/2008 |
| CN | 101368297 | 2/2009 |
| CN | 101397394 | 4/2009 |
| CN | 101608349 | 12/2009 |
| CN | 101608350 | 12/2009 |
| CN | 101759969 | 6/2010 |

(Continued)

OTHER PUBLICATIONS

"Epoxidized Oils and Derivatives," UNEP Publications, Jan. 20, 2006; 173 pages.
Al-Mulla, "Properties of Epoxidized Palm Oil Plasticized Polytlactic Acid," Journal of Material Science, Apr. 2010; vol. 45, No. 7, pp. 1942-1946.
Garlotta, "A Literature Review of Poly (Lactic Acid)", Journal of Polymers and the Environment, Apr. 2001, vol. 9, No. 2, pp. 63-84.
Kricheldorf, Syntheses and Application of Polyactides,' Chemosphere, 2001; vol. 43, No. 1, pp. 49-54.
Leenslag, "Resorbable Materials of Poly (L-lactide). V. Influence of Secondary Structure on the Mechanical Properties and Hydrolyzability of Poly(L-lactide) Fibers Produced by a Dry-Spinning Method," Journal of Applied Polymer Science, 1984, vol. 29, No. 9, pp. 2829-2842.

(Continued)

*Primary Examiner* — Ernst V Arnold

(57) ABSTRACT

Fibers, which can be used for making wipes (e.g., antimicrobial wipes), wherein the include: an aliphatic polyester; an unreacted epoxidized fatty ester having greater than 4.7 wt-% oxirane oxygen, based on the total weight of the epoxidized fatty ester; wherein the aliphatic polyester and unreacted epoxidized fatty ester form a mixture.

16 Claims, No Drawings

(56) References Cited

FOREIGN PATENT DOCUMENTS

| | | |
|---|---|---|
| CN | 101914272 | 12/2010 |
| CN | 102286801 | 12/2011 |
| DE | 10349168 | 6/2005 |
| EP | 1544331 | 6/2005 |
| JP | 2001-271250 | 10/2001 |
| JP | 2009-249450 | 10/2009 |
| JP | 2011-256221 | 12/2011 |
| JP | 2011-256221 A | 12/2011 |
| WO | WO 1984-04311 | 11/1984 |
| WO | WO 1994-07949 | 4/1994 |
| WO | WO 1996-022330 | 7/1996 |
| WO | WO 1997-19991 | 6/1997 |
| WO | WO 1998-24951 | 6/1998 |
| WO | WO 1998-50611 | 11/1998 |
| WO | WO 1999-06456 | 2/1999 |
| WO | WO 1999-50345 | 10/1999 |
| WO | WO 2000-12606 | 3/2000 |
| WO | WO 2003-040201 | 5/2003 |
| WO | WO 2008-073101 | 6/2008 |
| WO | WO 2009-151439 | 12/2009 |
| WO | WO 2009-152345 | 12/2009 |
| WO | WO 2009-152349 | 12/2009 |
| WO | WO 2010-117612 | 10/2010 |
| WO | WO 2011-075619 | 6/2011 |
| WO | WO 2011-084670 | 7/2011 |
| WO | WO 2015-047890 | 4/2015 |
| WO | WO 2015-047988 | 4/2015 |

OTHER PUBLICATIONS

Resconi, "Selectivity in Propene Polymerization with Metallocene Catalysts," Chemical Reviews, 2000, vol. 100, No. 4, pp. 1253-1345.
Xu "Mechanical and Rheological Properties of Epoxidized Soybean Oil Plasticized Poly (lactic acid)," Journal of Applied Polymer Science, 2009, vol. 112, pp. 3185-3191.
International Search report for PCT International Application No. PCT/US2014/055981 dated Jan. 23, 2015, 4 pages.

FIBERS, WIPES, AND METHODS

BACKGROUND

There is a trend to manufacture products from renewable resources for global environmental protection. Aliphatic polyesters from renewable resources have found increasing application in materials because of their biodegradability and compostability, such as poly(lactic acid); however, such materials may not have suitable shelf-life stability for certain applications, particularly in environments of high moisture content due to degradation from hydrolysis. For extended hydrolytic stability of these aliphatic polyesters, reactive additives are commonly used to crosslink terminal —OH and/or —$CO_2H$ groups as one of the approaches. This may significantly change the molecular weight of the original aliphatic polyester, which may affect its processability and properties. Thus, there is a need for hydrolytic stabilization of aliphatic polyesters without reaction between the stabilizer and the aliphatic polyesters.

SUMMARY OF THE DISCLOSURE

The present disclosure provides fibers, which can be used for making wipes such as wet wipes for cleaning and/or disinfecting (e.g., antimicrobial wipes). The fibers include aliphatic polyesters and one or more additives that improve the hydrolytic stability of the fibers.

In one embodiment, the present disclosure provides a fiber that includes: an aliphatic polyester; and an unreacted epoxidized fatty ester having greater than 4.7 wt-% oxirane oxygen, based on the total weight of the epoxidized fatty ester; wherein the aliphatic polyester and epoxidized fatty ester form a mixture; and wherein the unreacted epoxidized fatty ester is present in an amount of at least 0.5 wt-%, based on the total weight of the mixture (i.e., the aliphatic polyester, epoxidized fatty ester, and shrink reduction additive (if present), and other optional additives).

In certain embodiments, the aliphatic polyester is selected from the group of poly(lactide), poly(glycolide), poly(lactide-co-glycolide), poly(L-lactide-co-trimethylene carbonate), poly(dioxanone), poly(butylene succinate), poly(butylene adipate), poly(ethylene adipate), polyhydroxybutyrate, polyhydroxyvalerate, and blends and copolymers thereof.

In another embodiment, the present disclosure provides a wet wipe that includes: a web of fibers (i.e., a fibrous web) as described herein; and an aqueous composition in contact with the web of fibers, wherein the aqueous composition includes water and a surfactant and/or a biocide (dissolved or dispersed in the water). The aqueous composition may also include one or more organic solvents, such as alcohols (e.g., isopropanol), along with the water.

In yet another embodiment, the present disclosure provides a wet wipe that includes: a fibrous web including fibers that include: an aliphatic polyester; and an unreacted epoxidized fatty ester having greater than 4.7 wt-% oxirane oxygen, based on the total weight of the epoxidized fatty ester; wherein the aliphatic polyester and epoxidized fatty ester form a mixture; and wherein the unreacted epoxidized fatty ester is present in an amount of at least 0.5 wt-%, based on the total weight of the mixture; and an aqueous composition contacting the fibrous web, wherein the aqueous composition includes: water; and a surfactant and/or a biocide (dissolved or dispersed in the water).

In certain embodiments, the aqueous composition includes a surfactant, wherein the wet wipe is a cleaning wipe.

In certain embodiments, the aqueous composition includes a biocide, wherein the wet wipe is a disinfecting wipe.

In certain embodiments, the aqueous composition includes a biocide and a surfactant, wherein the wet wipe is a cleaning/disinfecting wipe.

In certain embodiments, the present disclosure provides a process for improving the hydrolytic stability of fibers that include an aliphatic polyester. The method includes: mixing components that include an aliphatic polyester and an epoxidized fatty ester to form a mixture; wherein the unreacted epoxidized fatty ester has at least 4.7 wt-% oxirane oxygen, based on the total weight of the epoxidized fatty ester; and wherein the unreacted epoxidized fatty ester is present in an amount of at least 0.5 wt-%, based on the total weight of the mixture; and forming fibers out of the mixture.

In certain embodiments, the mixture of the aliphatic polyester and epoxidized fatty ester also include a shrink reduction additive.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The words "preferred" and "preferably" refer to claims of the disclosure that may afford certain benefits, under certain circumstances. However, other claims may also be preferred, under the same or other circumstances. Furthermore, the recitation of one or more preferred claims does not imply that other claims are not useful, and is not intended to exclude other claims from the scope of the disclosure.

In this application, terms such as "a," "an," and "the" are not intended to refer to only a singular entity, but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

Also herein, all numbers are assumed to be modified by the term "about" and preferably by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used.

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

As used herein, the term "room temperature" refers to a temperature of about 20° C. to about 25° C. or about 22° C. to about 25° C.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

The present disclosure provides fibers (e.g., fibers for use in making wipes such as wet wipes), and methods of making the fibers. The wet wipes made from the fibers can be used as cleaning and/or disinfecting wipes (e.g., antimicrobial wipes such as antiviral and/or antibacterial and/or antifungal wipes). Significantly, wet wipes of the present disclosure have advantageous shelf-life stability.

Fibers of the present disclosure include an aliphatic polyester, an unreacted epoxidized fatty ester, and optionally a shrink reduction additive in the form of a mixture. In certain embodiments, fibers of the present disclosure include an epoxidized fatty ester, wherein the unreacted epoxidized fatty ester has greater than 4.7 wt-% oxirane oxygen, based on the total weight of the epoxidized fatty ester; and an optional shrink reduction additive; wherein the unreacted epoxidized fatty ester is present in an amount of at least 0.5 wt-%, based on the total weight of the mixture (i.e., the aliphatic polyester, epoxidized fatty ester, and shrink reduction additive (if present), and other optional additives).

Such components of the fibers (the aliphatic polyester, epoxidized fatty ester, and optional shrink reduction additive) are in the form of mixtures, which can be a blend, a compounded mixture, or the like, wherein the unreacted epoxidized fatty ester is uniformly distributed or dispersed within the aliphatic polyester. That is, the unreacted epoxidized fatty ester and the aliphatic polyester are not noticeably reacted with each other such that chemical bonds are formed. That is, relative to the aliphatic polyester, the epoxidized fatty ester is "unreacted."

Herein, an unreacted epoxidized fatty ester is one that does not noticeably react with the aliphatic polyester during normal thermal processing and does not noticeably increase the molecular weight of the aliphatic polyester or the corresponding viscosity of the mixture. In this context, an "unreacted" epoxidized fatty ester is one that remains in a "free" or unreacted state when in the mixture with the aliphatic polyester (even after thermal processing) in an amount of at least 80%, or at least 90%, or at least 95%, of the unreacted epoxidized fatty ester based on the analysis by Gel Permeation Chromatography (GPC) of the solution of the thermal processed mixture.

Thus, the present disclosure provides a process for improving the hydrolytic stability of fibers that include an aliphatic polyester. The method includes: mixing components that include an aliphatic polyester with an unreacted epoxidized fatty ester, and an optional shrink reduction additive; wherein the unreacted epoxidized fatty ester has at least 4.7 wt-% oxirane oxygen, based on the total weight of the epoxidized fatty ester; and wherein the unreacted epoxidized fatty ester is present in an amount of at least 0.5 wt-%, based on the total weight of the mixture (e.g., aliphatic polyester, epoxidized fatty ester, and shrink reduction additive (if present)); and forming fibers out of the mixture. In forming such mixture, there is no noticeable reaction between the aliphatic polyester and epoxidized fatty ester.

Mixtures of the components can be made into fibers by various techniques, including, but not limited to, co-extrusion, solvent-based methods, and melt processing techniques such as melt-blown and spunbond processes. Exemplary fibers are melt-blown and spunbond fibers.

In certain embodiments, the fibers are continuous fibers that form a web (i.e., a network of entangled fibers forming a sheet like or fabric like structure), particularly a nonwoven web (i.e., an assembly of polymeric fibers (oriented in one direction or in a random manner) held together by mechanical interlocking, fusing of thermoplastic fibers, bonding with a suitable binder such as a natural or synthetic polymeric resin, or a combination thereof).

Webs made from the fibers can be woven, nonwoven, or knitted webs. The fibers can include fibers of indefinite length (e.g., filaments), fibers of discrete length (e.g., staple fibers), and multifilament yarns. Suitable manufacturing processes for making nonwoven webs include, but are not limited to, carding, meltblown, wet laid, air laid, or spunbond. The webs can be single layer or multi-layer constructions, such as SMS (Spunbond, Meltblown, Spunbond) or SMMS webs.

The general methods of making spunbond nonwoven fabric are well known in the art. An exemplary process of making spunbond nonwoven webs is described in U.S. Pat. No. 7,470,389 (Berrigan et al.). Generally, a stream of filaments is extruded from a spin-pack having multiple orifices arranged in a regular pattern and directed through a processing chamber. The stream of filaments are subsequently cooled and stretched with high speed air jets and deposited onto a collecting belt in a random manner. The collecting belt is generally porous. A vacuum device can be positioned below the collecting belt to assist the fiber deposition onto the collecting belt. The collected mass (web) can be imparted strength and integrity by thermal bonding (e.g., applying heated rolls or passing hot air through) to partially melt the polymer and fuse the fibers together. The web can be further bonded to improve strength and other properties by mechanical bonding processes such as hydroentangling as described, for example, in U.S. Pat. No. 4,808,467 (Israel et al.).

In certain embodiments, the fibers made using compositions of the present disclosure are fine fibers, wherein a population of such fibers has a median fiber diameter of no greater than 50 μm, or no greater than 25 μm, or no greater than 20 μm, or no greater than 10 μm, or no greater than 5 μm. In certain embodiments, the fibers are microfibers, wherein a population of such fibers has a median fiber diameter of at least one μm but no greater than 100 μm. In certain embodiments, the fibers are ultrafine microfibers, wherein a population of such fibers has a median fiber diameter of two μm or less. In certain embodiments, the fibers are sub-micrometer fibers, wherein a population of such fibers has a median fiber diameter of no greater than one μm.

The presence of an epoxidized fatty ester additive in aliphatic polyester webs improves the hydrolytic stability of the aliphatic polyester, and hence, the "shelf life" of the fibers.

An improvement in the hydrolytic stability of fibers that include an aliphatic polyester can be demonstrated by an improvement in the tensile strength of the fibers forming a web, and optionally the dimensional stability (e.g., if a shrink reduction additive is present) of the fibers forming a web, particularly after aging in an aqueous medium.

Typically, improvement in tensile strength means that a web made of fibers of the present disclosure demonstrates greater than 10% increase in tensile strength after aging at a temperature of 135° F. for at least 25 days (in an aqueous cleaning and/or disinfecting solution as exemplified in the Examples Section), compared to a web made of fibers of the same aliphatic polyester without such additives.

Typically, improvement in dimensional stability means that a web made of fibers of the present disclosure has at least one dimension which shrinks by no greater than 10% (preferably, no greater then 5%) in the plane of the web when the web is heated to a temperature above a glass transition temperature of the fibers, but below the melting point of the fibers in an unrestrained (i.e., free to move) condition, as compared to a web made of fibers of the same aliphatic polyester without such additives.

In certain situations, compositions of the present disclosure may have shrinkage problems since epoxidized fatty esters, such as epoxidized vegetable oils, are well known as plasticizers that can significantly reduce the crystallinity of an aliphatic polyester. The addition of an optional shrinkage reduction additive can thus provide a balance of properties by providing a reduction in shrinkage. Typically, reduction in shrinkage means a demonstration of greater than 5% decrease in shrinkage compared to a web made of fibers of the same aliphatic polyester and epoxidized fatty ester combination without such shrink reduction additive.

Aliphatic Polyesters

Aliphatic polyesters useful in embodiments of the present disclosure include homo- and co-polymers of poly(hydroxyalkanoates), and homo- and co-polymers of those aliphatic polyesters derived from the reaction product of one or more polyols with one or more polycarboxylic acids that is typically formed from the reaction product of one or more alkanediols with one or more alkanedicarboxylic acids (or acyl derivatives). Aliphatic polyesters may further be derived from multifunctional polyols, e.g. glycerin, sorbitol, pentaerythritol, and combinations thereof, to form branched, star, and graft homo- and co-polymers.

Exemplary aliphatic polyesters are poly(lactic acid), poly(glycolic acid), poly(lactic-co-glycolic acid), polybutylene succinate, polyethylene adipate, polyhydroxybutyrate, polyhydroxyvalerate, blends, and copolymers thereof. One particularly useful class of aliphatic polyesters are poly(hydroxyalkanoates), derived by condensation or ring-opening polymerization of hydroxy acids, or derivatives thereof. Suitable poly(hydroxyalkanoates) may be represented by the Formula (I):

(I)

wherein: R is an alkylene moiety that may be linear or branched having 1 to 20 carbon atoms, preferably having 1 to 12 carbon atoms, more preferably having 1 to 6 carbon atoms; and n is a number such that the ester is polymeric, and is preferably a number such that the molecular weight of the aliphatic polyester is at least 8,000 daltons (Da).

In Formula (I), R may further include one or more catenary (i.e., in chain) ether oxygen atoms. That is, R may optionally be substituted by catenary (bonded to carbon atoms in a carbon chain) oxygen atoms. Generally, the R group of the hydroxy acid is such that the pendant hydroxyl group is a primary or secondary hydroxyl group.

Useful poly(hydroxyalkanoates) include, for example, homo- and copolymers of poly(3-hydroxybutyrate), poly(4-hydroxybutyrate), poly(3-hydroxyvalerate), poly(lactic acid) (as known as polylactide), poly(3-hydroxypropanoate), poly(4-hydroxypentanoate), poly(3-hydroxypentanoate), poly(3-hydroxyhexanoate), poly(3-hydroxyheptanoate), poly(3-hydroxyoctanoate), polydioxanone, polycaprolactone, and polyglycolic acid (i.e., polyglycolide).

Copolymers of two or more of the above hydroxy acids may also be used, for example, poly(3-hydroxybutyrate-co-3-hydroxyvalerate), poly(lactate-co-3-hydroxypropanoate), poly(glycolide-co-dioxanone), and poly(lactic acid-co-glycolic acid).

Blends of two or more of the poly(hydroxyalkanoates) may also be used, as well as blends (miscible or immiscible) with one or more other polymers and/or copolymers.

Aliphatic polyesters useful in the disclosure may include homopolymers, random copolymers, block copolymers, star-branched random copolymers, star-branched block copolymers, dendritic copolymers, hyperbranched copolymers, graft copolymers, and combinations thereof.

Another useful class of aliphatic polyesters includes those aliphatic polyesters derived from the reaction product of one or more alkanediols with one or more alkanedicarboxylic acids (or acyl derivatives). Such polyesters have the general Formula (II):

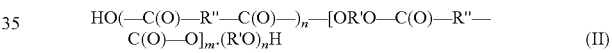

(II)

wherein: R' and R'' each represent an alkylene moiety that may be linear or branched having from 1 to 20 carbon atoms, preferably 1 to 12 carbon atoms; m is a number such that the ester is polymeric, and is preferably a number such that the molecular weight of the aliphatic polyester is at least 8,000 daltons (Da); and each n is independently 0 or 1.

In Formula (II), R' and R'' may further include one or more catemary (i.e., in chain) ether oxygen atoms. Examples of aliphatic polyesters include those homo- and co-polymers derived from (a) one or more of the following diacids (or derivative thereof): succinic acid; adipic acid; 1,12 dicarboxydodecane; fumaric acid; glutartic acid; diglycolic acid; and maleic acid; and (b) one of more of the following diols: ethylene glycol; 30 polyethylene glycol; 1,2-propane diol; 1,3-propanediol; 1,2-propanediol; 1,2-butanediol; 1,3-butanediol; 1,4-butanediol; 2,3-butanediol; 1,6-hexanediol; 1,2-alkane diols having 5 to 12 carbon atoms; diethylene glycol; polyethylene glycols having a molecular weight of 300 to 10,000 daltons, preferably 400 to 8,000 daltons; propylene glycols having a molecular weight of 300 to 4000 daltons; block or random copolymers derived from ethylene oxide, propylene oxide, or butylene oxide; dipropylene glycol; and polypropylene glycol, and (c) optionally a small amount (i.e., 0.5-7.0 mole-%) of a polyol with a functionality greater than two such as glycerol, neopentyl glycol, and pentaerythritol. Such polymers may include polybutylene succinate homopolymer, polybutylene adipate homopolymer, polybutylene adipate-succinate copolymer, polyethylene succinate-adipate copolymer, polyethylene glycol succinate homopolymer and polyethylene adipate homopolymer.

Commercially available aliphatic polyesters include poly (lactide), poly(glycolide), poly(lactide-co-glycolide), poly (L-lactide-co-trimethylene carbonate), poly(dioxanone), poly(butylene succinate), and poly(butylene adipate).

Preferred aliphatic polyesters include those derived from semicrystalline polylactic acid. Poly(lactic acid) or polylactide has lactic acid as its principle degradation product, which is commonly found in nature, is non-toxic and is widely used in the food, pharmaceutical and medical industries. The polymer may be prepared by ring-opening polymerization of the lactic acid dimer, lactide. Lactic acid is optically active and the dimer appears in four different forms: L,L-lactide, D,D-lactide, D,L-lactide (meso lactide) and a racemic mixture of L,L- and D,D-. By polymerizing these lactides as pure compounds or as blends, poly(lactide) polymers may be obtained having different stereochemistries and different physical properties, including crystallinity. The L,L- or D,D-lactide yields semicrystalline poly (lactide), while the poly(lactide) derived from the D,L-lactide is amorphous. The polylactide preferably has a high enantiomeric ratio to maximize the intrinsic crystallinity of the polymer. The degree of crystallinity of a poly(lactic acid) is based on the regularity of the polymer backbone and the ability to crystallize with other polymer chains. If relatively small amounts of one enantiomer (such as D-) is copolymerized with the opposite enantiomer (such as L-) the polymer chain becomes irregularly shaped, and becomes less crystalline. For these reasons, when crystallinity is favored, it is desirable to have a poly(lactic acid) that is at least 85% of one isomer, more preferably at least 90% of one isomer, or even more preferably at least 95% of one isomer in order to maximize the crystallinity. An approximately equimolar blend of D-polylactide and L-polylactide is also useful. This blend forms a unique crystal structure having a higher melting point (approximately 210° C.) than does either the D-poly(lactide) and L-poly(lactide) alone (approximately 160° C.), and has improved thermal stability, see H. Tsuji et al., *Polymer*, 40 (1999) 6699-6708.

Copolymers, including block and random copolymers, of poly(lactic acid) with other aliphatic polyesters may also be used. Useful co-monomers include glycolide, beta-propiolactone, tetramethylglycolide, beta-butyrolactone, gamma-butyrolactone, pivalolactone, 2-hydroxybutyric acid, alpha-hydroxyisobutyric acid, alpha-hydroxyvaleric acid, alpha-hydroxyisovaleric acid, alpha-hydroxycaproic acid, alpha-hydroxyethylbutyric acid, alpha-hydroxyisocaproic acid, alpha-hydroxy-betamethylvaleric acid, alpha-hydroxyoctanoic acid, alpha-hydroxydecanoic acid, alpha-hydroxymyristic acid, and alpha-hydroxystearic acid. Blends of poly(lactic acid) and one or more other aliphatic polyesters, or one or more other polymers may also be used. Examples of useful blends include poly(lactic acid) with a second polymer selected from poly(vinyl alcohol), polyethylene glycol, polysuccinate, polyethylene oxide, polycaprolactone and polyglycolide.

Poly(lactide)s may be prepared as described in U.S. Pat. No. 6,111,060 (Gruber, et al.), U.S. Pat. No. 5,997,568 (Liu), U.S. Pat. No. 4,744,365 (Kaplan et al.), U.S. Pat. No. 5,475,063 (Kaplan et al.), U.S. Pat. No. 6,143,863 (Gruber et al.), U.S. Pat. No. 6,093,792 (Gross et al.), U.S. Pat. No. 6,075,118 (Wang et al.), U.S. Pat. No. 5,952,433 (Wang et al.), U.S. Pat. No. 6,117,928 (Hiltunen et al.), U.S. Pat. No. 5,883,199 (McCarthy et al.), and International Publication Nos. WO 98/124951 (Tsai et al.), WO 00/112606 (Tsai et al.), WO 84/04311 (Lin), WO 99/50345 (Kolstad et al.), WO 99/06456 (Wang et al.), WO 94/07949 (Gruber et al.), WO 96/122330 (Randall et al.), and WO 98/50611 (Ryan et al.), for example. Reference may also be made to J. W. Leenslag et al., *J. Appl. Polymer Science*, vol. 29 (1984), pp 2829-2842, and H. R. Kricheldorf, *Chemosphere*, vol. 43 (2001) 49-54.

The molecular weight of the polymer should be chosen so that the polymer may be processed as a melt. By "melt-processible," it is meant that the aliphatic polyesters are fluid or can be pumped or extruded at the temperatures used to process the fibers, and do not degrade or gel at those temperatures to the extent that the physical properties are so poor as to be unusable for the intended application. Thus, many of the materials can be made into nonwovens using melt processes such as spun bond, blown microfiber, and the like. Certain embodiments also may be injection molded.

In certain embodiments, the molecular weight (number average) of suitable aliphatic polyesters is at least 8,000, or at least 10,000, or at least 30,000, or at least 50,000 daltons. Although higher molecular weight polymers generally yield films with better mechanical properties, for both melt processed and solvent cast polymers excessive viscosity is typically undesirable. The molecular weight of the aliphatic polyester is typically no greater than 1,000,000, preferably no greater than 500,000, and most preferably no greater than 300,000 daltons (Da), as measured by gel permeation chromatography (GPC).

For a poly(lactide), for example, the molecular weight may be from 8,000 to 1,000,000 daltons, and is preferably from 30,000 to 300,000 daltons (Da).

The aliphatic polyester may be blended with other polymers but typically is present in fibers of the present disclosure in an amount of at least 50 weight percent, or at least 60 weight percent, or at least 65 weight percent, or at least 80 weight percent (wt-%) of the fibers of the present disclosure.

Epoxidized Fatty Esters

Epoxidized fatty esters, such as epoxidized vegetable oils, are commonly known as plasticizers for easy thermal processing of polymers (or processing aides). Suitable epoxidized fatty esters for use in fibers of the present disclosure are used as hydrolysis stabilizing agents. That is, suitable epoxidized fatty esters are those capable of improving the hydrolytic stability of fibers that include an aliphatic polyester, but without noticeable reaction with the aliphatic polyester during mixing, and even during thermal processing, such as compounding and extrusion processing. That is, there is no significant reaction that occurred between the epoxidized fatty ester and the aliphatic polyester such that there is a noticeable increase in the molecular weight of the aliphatic polyester and the corresponding viscosity of the mixture. Specifically, a mixture of an epoxidized fatty ester and an aliphatic polyester, particularly one that is thermally processed, includes at least 80%, or at least 90%, or at least 95%, of free (unreacted) epoxidized fatty ester (based on the GPC analysis).

Even though there is little or no reaction (e.g., crosslinking) between the aliphatic polyester and the epoxidized fatty ester, particularly during thermal processing, the presence of the free epoxidized fatty esters in the presence of the aliphatic polyester reduces the hydrolysis rate when the compounded aliphatic polyester is aged or dispersed into a water-based medium for a long period of time. This occurs typically by reducing the hydrolysis speed of the aliphatic polyester by the unreacted epoxidized fatty esters.

Although not wishing to be bound by theory, it is believed that as the aliphatic polyester starts to hydrolyze in an aqueous environment, more carboxylic acid groups are formed in the aliphatic polyester that results in an increase in acidity (lower pH). As the hydrolysis continues, the epoxy group of the epoxidized fatty ester tends to react with the carboxylic acid group of the aliphatic polyester. As such, the epoxidized fatty ester acts as a crosslinker for the hydrolyzable aliphatic polyester, which results in the formation of a higher molecular weight polymer network. At the same time, the reaction that occurs between the epoxy groups of epoxidized fatty ester and the carboxylic acid groups of the aliphatic polyester that are formed during hydrolysis actually neutralizes the pH of the aliphatic polyester. This results in a slowdown of the hydrolysis of the aliphatic polyester that correspondingly leads to an increased shelf life of the aliphatic polyester in aqueous media. From this aforementioned theory, it is suggested that a higher oxirane oxygen of the epoxidized fatty ester will tend to greatly increase the hydrolytic stability of an aliphatic polyester such as poly (lactic acid).

Fibers of the present disclosure typically include an epoxidized fatty ester that has greater than 4.7 wt-% oxirane oxygen, based on the total weight of the epoxidized fatty ester. In certain embodiments, the amount of oxirane oxygen is at least 5.5 wt-%, at least 6 wt-%, or at least 9 wt-%, oxirane oxygen, based on the total weight of the epoxidized fatty ester. In certain embodiments, the amount of oxirane oxygen is up to 23 wt-%, or up to 11 wt-%, oxirane oxygen, based on the total weight of the epoxidized fatty ester. In certain embodiments, the amount of oxirane oxygen is 6 wt-% to 11 wt-% oxirane oxygen, based on the total weight of the epoxidized fatty ester.

In certain embodiments, the epoxidized fatty ester is an epoxidized poly(fatty ester) (i.e., a di- or tri-ester or higher functional ester). In certain embodiments, the epoxidized vegetable oil includes a di-ester, tri-ester, or combinations thereof. In certain embodiments, the epoxidized vegetable oil includes a tri-ester or higher functional ester.

In certain embodiments, the epoxidized fatty ester is a triglyceride of an epoxidized polyunsaturated fatty acid. The epoxidized polyunsaturated fatty acid can be made from the epoxidation of a triglyceride of a polyunsaturated fatty acid, wherein the triglyceride of a polyunsaturated fatty acid can be made from the estification of glycerol and a polyunsaturated fatty acid. Preferably, the polyunsaturated fatty acid has two or more unsaturated double bonds for higher amounts of oxirane oxygen resulting from an epoxidization process. In certain embodiments, the polyunsaturated fatty acid is selected from linoleic acid, linoelaidic acid, α-linolenic acid, arachidonic acid, eicosapentaenoic acid, docosahexaenoic acid, and combinations thereof. The chemical structures of such preferred polyunsaturated fatty acids are shown in the following table.

In certain embodiments, the epoxidized fatty ester is an epoxidized vegetable oil. In certain embodiments, the epoxidized vegetable oil is selected from the group of epoxidized soybean oil, epoxidized cottonseed oil, epoxidized wheat germ oil, epoxidized soya oil, epoxidized corn oil, epoxidized sunflower oil, epoxidized safflower oil, epoxidized hemp oil, epoxidized linseed oil, and combinations thereof.

In certain embodiments, the vegetable oil used for preparation of the epoxidized vegetable oil has a polyunsaturated value of at least 50 grams per 100 grams total oil, preferably at least 60 grams per 100 grams total oil. The polyunsaturated value is the weight of the polyunsaturated oil in 100 grams of total oil (100 g of saturated oil+monounsaturated oil+polyunsaturated oil). The polyunsaturated values of various oils, useful for making epoxidized vegetable oils, are shown in the following table, which shows that examples of epoxidized vegetable oil having a polyunsaturated value of at least approximately 50 grams per 100 grams total oil include wheat germ sunflower oil, safflower oil, and hemp oil.

| Oil | Saturated g/100 g | Monounsaturated g/100 g | Polyunsaturated g/100 g |
| --- | --- | --- | --- |
| Cottonseed oil | 25.5 | 21.3 | 48.1 |
| Wheat germ oil | 18.8 | 15.9 | 60.7 |
| Soya oil | 14.5 | 23.2 | 56.5 |
| Corn oil | 12.7 | 24.7 | 57.8 |
| Sunflower oil | 11.9 | 20.2 | 63.0 |
| Safflower oil | 10.2 | 12.6 | 72.1 |
| Hemp oil | 10 | 15 | 75 |

In certain embodiments, compositions of the present disclosure (i.e., mixtures) typically include at least 1 wt-%, or at least 2 wt-%, or at least 3 wt-%, or at least 5 wt-%, of an epoxidized fatty ester, based on the total weight of the mixture (i.e., the aliphatic polyester, epoxidized fatty ester, and shrink reduction additive (if present), and other optional additives). In certain embodiments, fibers of the present disclosure typically include up to 20 wt-%, or up to 10 wt-%, of an epoxidized fatty ester, based on the total weight of the mixture. In certain embodiments, fibers of the present disclosure typically include up to 7 wt-% (and in some embodiments, less than 7 wt-%), or up to 6 wt-%, of an epoxidized fatty ester, based on the total weight of the mixture.

Optional Shrink Reduction Additives

The "shrink reduction" or "antishrink" or "antishrinkage" additive (i.e., agent) refers to a thermoplastic polymeric additive which, when added to the aliphatic polyester in a suitable amount during thermal process formation of a uniform fibrous web, results in a web having at least one dimension which shrinks by no greater than 10% in the plane of the web when the web is heated to a temperature above a glass transition temperature of the fibers, but below the

| Common name | Chemical structure |
| --- | --- |
| Linoleic acid | $CH_3(CH_2)_4CH=CHCH_2CH=CH(CH_2)_7COOH$ (9E,9E) |
| Linoelaidic acid | $CH_3(CH_2)_4CH=CHCH_2CH=CH(CH_2)_7COOH$ (9Z,9Z) |
| α-Linolenic acid | $CH_3CH_2CH=CHCH_2CH=CHCH_2CH=CH(CH_2)_7COOH$ |
| Arachidonic acid | $CH_3(CH_2)_4CH=CHCH_2CH=CHCH_2CH=CHCH_2CH=CH(CH_2)_3COOH$ |
| Eicosapentaenoic acid | $CH_3CH_2CH=CHCH_2CH=CHCH_2CH=CHCH_2CH=CHCH_2CH=CH(CH_2)_3COOH$ |
| Docosahexaenoic acid | $CH_3CH_2CH=CHCH_2CH=CHCH_2CH=CHCH_2CH=CHCH_2CH=CH(CH_2)_2COOH$ | melting point of the fibers in an unrestrained (free to move) state, when compared to a web made in the same way with the same components without the shrink reduction additive.

Preferred shrink reduction additives (i.e., shrink reduction agents) form a dispersed phase in the aliphatic polyester when the mixture is cooled to 23-25° C. Preferred shrink reduction additives are also semicrystalline thermoplastic polymers as determined by differential scanning calorimetry.

Potentially useful semicrystalline polymers include polyethylene, linear low density polyethylene, polypropylene, polyoxymethylene, poly(vinylidine fluoride), poly(methyl pentene), poly(ethylene-chlorotrifluoroethylene), poly(vinyl fluoride), poly(ethylene oxide) (PEO), poly(ethylene terephthalate), poly(butylene terephthalate), semicrystalline aliphatic polyesters including polycaprolactone (PCL), aliphatic polyamides such as nylon 6 and nylon 66, thermotropic liquid crystal polymers, and combinations thereof. Particularly preferred semicrystalline polymers include polypropylene, nylon 6, nylon 66, polycaprolactone, and poly(ethylene oxide).

The shrink reduction additives have been shown to dramatically reduce the shrinkage of PLA nonwovens. The molecular weight (MW) of these additives may affect the ability to promote shrinkage reduction. Preferably the MW is greater than about 10,000 daltons, preferably greater than 20,000 daltons, more preferably greater than 40,000 daltons and most preferably greater than 50,000 daltons.

Derivatives of the thermoplastic shrink reduction polymers also may be suitable. Preferred derivatives will likely retain some degree of crystallinity. For example, polymers with reactive end groups such as PCL and PEO can be reacted to form, for example, polyesters or polyurethanes, thus increasing the average molecular weight.

A highly preferred shrink reduction additive is a polyolefin, in particular a polypropylene. Polypropylene homo- and co-polymers useful in practicing embodiments of the present disclosure may be selected from polypropylene homopolymers, polypropylene copolymers, and blends thereof (collectively polypropylene polymers). The homopolymers may be atactic polypropylene, isotactic polypropylene, syndiotactic polypropylene and blends thereof. The copolymer can be a random copolymer, a statistical copolymer, a block copolymer, and blends thereof. In particular, the polymer blends described herein include impact copolymers, elastomers and plastomers, any of which may be physical blends or in situ blends with the polypropylene.

The polypropylene polymers can be made by any method known in the art such as by slurry, solution, gas phase or other suitable processes, and by using catalyst systems appropriate for the polymerization of polyolefins, such as Ziegler-Natta-type catalysts, metallocene-type catalysts, other appropriate catalyst systems or combinations thereof. In a preferred embodiment, the propylene polymers are made by the catalysts, activators and processes described in U.S. Pat. No. 6,342,566 (Burkhardt et al.); U.S. Pat. No. 6,384,142 (Burkhardt et al.); WO 03/040201 (Stevens et al.); WO 97/19991 (McAlpin et al.) and U.S. Pat. No. 5,741,563 (Mehta et al.). Likewise, the polypropylene polymers may be prepared by the process described in U.S. Pat. Nos. 6,342,566 and 6,384,142. Such catalysts are well known in the art, and are described in, for example, ZIEGLER CATALYSTS (Gerhard Fink, Rolf Mulhaupt and Hans H. Brintzinger, eds., Springer-Verlag 1995); Resconi et al., Selectivity in Propene Polymerization with Metallocene Catalysts, 100 CHEM. REV. 20 1253-1345 (2000); and I, II METALLOCENE-BASED POLYOLEFINS (Wiley & Sons 2000).

Propylene polymers that are useful in practicing some embodiments of the present disclosure include those sold under the tradenames ACHIEVE and ESCORENE by Exxon-Mobil Chemical Company (Houston, Tex.), and various propylene (co)polymers sold by Total Petrochemicals (Houston, Tex.).

Presently preferred propylene homopolymers and copolymers useful in the present disclosure typically have: 1) a weight average molecular weight (Mw) of at least 30,000 Da, preferably at least 50,000 Da, more preferably at least 90,000 Da, as measured by gel permeation chromatography (GPC), and/or no more than 2,000,000 30 Da, preferably no more than 1,000,000 Da, more preferably no more than 500,000 Da, as measured by gel permeation chromatography (GPC); and/or 2) a polydispersity (defined as Mw/Mn, wherein Mn is the number average molecular weight determined by GPC) of 1, preferably 1.6, and more preferably 1.8, and/or no more than 40, preferably no more than 20, more preferably no more than 10, and even more preferably no more than 3; and/or 3) a melting temperature Tm (second melt) of at least 30° C., preferably at least 50° C., and more preferably at least 60° C. as measured by using differential scanning calorimetry (DSC), and/or no more than 200° C., preferably no more than 185° C., more preferably no more than 175° C., and even more preferably no more than 170° C. as measured by using differential scanning calorimetry (DSC); and/or a crystallinity of at least 5%, preferably at least 10%, more preferably at least 20% as measured using DSC, and/or no more than 80%, preferably no more than 70%, more preferably no more than 60% as measured using DSC; and/or 5) a glass transition temperature (Tg) of at least −40° C., preferably at least −10° C., more preferably at least −10° C., as measured by dynamic mechanical thermal analysis (DMTA), and/or no more than 20° C., preferably no more than 10° C., more preferably no more than 5° C., as measured by dynamic mechanical thermal analysis (DMTA); and/or 6) a heat of fusion (Rf) of 180 J/g or less, preferably 150 J/g or less, more preferably 120 J/g or less as measured by DSC and/or at least 20 J/g, more preferably at least 40 J/g as measured by DSC; and/or 7) a crystallization temperature (Tc) of at least 15° C., preferably at least 20° C., more preferably at least 25° C., even more preferably at least 60° C. and/or, no more than 120° C., preferably no more than 115° C., more preferably no more than 110° C., even more preferably no more than 145° C.

Fibers of the present disclosure can optionally include a shrink reduction additive (preferably a propylene polymer (including both poly(propylene) homopolymers and copolymers)) in an amount of up to 10 wt-%, based on the total weight of the mixture of components used to make the fibers (i.e., aliphatic polyester, epoxidized fatty ester, and shrink reduction additive (if present), and other optional additives). In certain embodiments, fibers of the present disclosure include a shrink reduction additive in an amount of at least 0.5 wt-%, or at least 1 wt-%, or at least 2 wt-%, based on the total weight of the mixture of components used to make the fibers. In certain embodiments, fibers of the present disclosure include a shrink reduction additive (preferably a propylene polymer (including both poly(propylene) homopolymers and copolymers)) in an amount of up to 5 wt-%, based on the total weight of the mixture used to make the fibers.

Optional Additives

Various optional additives may be added to the fibers of the present disclosure. Suitable additives include, but are not limited to, particulates, fillers, stabilizers, plasticizers, tackifiers, flow control agents, cure rate retarders, adhesion promoters (for example, silanes and titanates), adjuvants, impact modifiers, expandable microspheres, thermally conductive particles, electrically conductive particles, silica, glass, clay, talc, pigments, colorants, glass beads or bubbles, antioxidants, optical brighteners, antimicrobial agents, surfactants, wetting agents, fire retardants, and repellents such as hydrocarbon waxes, silicones, and fluorochemicals. However, some fillers (i.e., insoluble organic or inorganic materials generally added to augment weight, size or to fill space in the resin for example to decrease cost or impart other properties such as density, color, impart texture, effect degradation rate and the like) may detrimentally effect fiber properties.

Fillers, if used, can be particulate non-thermoplastic or thermoplastic materials. Fillers also may be non-aliphatic polyesters polymers which often are chosen due to low cost such as starch, lignin, and cellulose based polymers, natural rubber, and the like. These filler polymers tend to have little or no crystallinity.

Fillers, plasticizers, and other additives, when used at levels above 3% by weight, and more certainly above 5% by weight of the aliphatic polyester, can have a significant negative effect on physical properties such as tensile strength of a web of the fibers. Above 10% by weight of the aliphatic polyester resin, these optional additives can have a dramatic negative effect on physical properties. Therefore, total optional additives are typically present at no more than 10% by weight, preferably no more than 5% by weight and most preferably no more than 3% by weight based on the weight of the aliphatic polyester.

Wet Wipes

Fibers of the present disclosure can be used in wipes, particularly wet wipes.

"Wet" wipe is a wipe wherein a substrate, typically a fibrous web (e.g., nonwoven web), has been pre-moistened with the aqueous composition. That is, the aqueous composition is in contact with the fibrous web. In most cases the wipe has been saturated with the aqueous composition (i.e., full absorbent capacity of the substrate used). But this may not necessarily have to be the case. It would depend on the absorbent capacity of the wipe and aqueous formulation. As long as the wipe can be loaded with enough active material, it would not have to be completely saturated. In some cases the wipes may be super-saturated, i.e., have more liquid than its absorbent capacity. This is achieved, for example, by delivering the wipes from a container with excess liquid composition.

Wet wipes are typically sold in sealed single-use or resealable multi-use packages or canisters often with an excess of the aqueous composition. "Wet" wipe also includes a wipe that is coated with a concentrate up to 100% solids that is subsequently wet with water by the user. For example, a roll of perforated wipes can be provided in a container to which the user adds a predetermined amount of water that wicks into the roll of wipes. In certain embodiments, the aqueous composition is present in an amount of at least 2 times, or at least 4 times, the weight of the fibrous web. In certain embodiments, the aqueous composition is present in an amount of up to 6 times, the weight of the fibrous web.

Herein, a wet wipe includes: a fibrous web as described herein and an aqueous composition that includes water and a surfactant and/or a biocide (dissolved or dispersed in the water). The aqueous composition may also include one or more organic solvents, such as alcohols (e.g., isopropanol), along with the water. The aqueous composition is in contact with the fibrous web.

For example, in certain embodiments, a wet wipe of the present disclosure includes a fibrous web including fibers that include: an aliphatic polyester; an unreacted epoxidized fatty ester having greater than 4.7 wt-% oxirane oxygen, based on the total weight of the epoxidized fatty ester; and an optional shrink reduction additive; wherein the aliphatic polyester, epoxidized fatty ester, and optional shrink reduction additive form a mixture; and wherein the unreacted epoxidized fatty ester is present in an amount of at least 0.5 wt-%, based on the total weight of the mixture (including aliphatic polyester, epoxidized fatty ester, shrink reduction additive (if present), and other optional additives).

The wet wipe also includes an aqueous composition that includes water and a surfactant and/or a biocide. The aqueous composition can have a pH of 1 to 14. In certain embodiments, the aqueous composition includes at least 0.01 wt-%, or at least 0.05 wt-%, surfactant and/or biocide, based on the total weight of the aqueous composition. In certain embodiments, the aqueous composition includes up to 0.5 wt-%, surfactant and/or biocide, based on the total weight of the aqueous composition.

In certain embodiments, the aqueous composition includes a surfactant and the wet wipe is a cleaning wipe.

In certain embodiments, the aqueous composition includes a biocide and the wet wipe is a disinfecting wipe.

In certain embodiments, the aqueous composition includes a biocide and a surfactant, wherein the wet wipe is a cleaning/disinfecting wipe.

The surfactant can be nonionic, anionic, cationic, amphoteric (i.e., zwitterionic), or combinations thereof. In certain embodiments, the surfactant is a nonionic surfactant.

Exemplary anionic surfactants include: alcohol sulfates and sulfonates, alcohol phosphates and phosphonates, alkyl sulfates, alkyl ether sulfate, sulfate esters of an alkylphenoxy polyoxyethylene ethanol, alkyl monoglyceride sulfate, alkyl sulfonate, alkyl benzene sulfonate, alkyl ether sulfonate, ethoxylated alkyl sulfonate, alkyl carboxylate, alkyl ether carboxylate, alkyl alkoxy carboxylate, alkane sulfonate, alkylbenzene sulfonate, alkyl ester sulfonate, alkyl sulfate, alkyl alkoxylated sulfate (e.g., sodium lauryl sulfate), alkyl carboxylate (e.g., sorbitan stearate), and sulfonated alkyl glucosides (e.g., sodium decylglucosides, hydroxypropyl sulfonate, sodium decylglucosides hydroxypropyl sulfonate and sodium laurylglucosides hydroxypropyl sulfonate).

Exemplary zwitteronic surfactants include Betaine and sultaine (e.g., C12-18 alkyl dimethyl betaines such as coco-nutbetaine), C10-C16 alkyl dimethyl betaine (laurylbetaine), fatty acylamidopropylene(hydroxylpropylene)sulfobetaine, lauryldimethylcarboxymethylbetaine, cocoamido propyl monosodium phosphitaine, cocoamido disodium 3-hydroxypropyl phosphobetaine, and amphoteric amine oxide (e.g., alkyl dimethyl amine oxides and alkylamidopropyl amine oxides).

Exemplary nonionic surfactants include ethoxylated alkylphenol, ethoxylated and propoxylated fatty alcohols, polyethylene glycol ethers of methyl glucose, ethoxylated esters of fatty acids, alkyl polyglucoside (e.g., capryl glucoside such as Glucopon 215UP, decyl glucoside such as Glucopon 225DK, coco-glucoside such as Glucopon 425N, lauryl glucoside such as Glucopon 625UP, an aqueous solution of alkyl glucosides based fatty acid alcohol C9-C11 such as APG 325N, and sodium laureth sulfate & lauryl glucoside & cocoamidopropyl betaine such as Plantapon 611L, fatty alcohol polyglycolether (e.g., Dephypon LS54, Dephypon LT104), fatty alcohol ethoxylates (propoxylates), and ethoxylated alkylphenol.

Exemplary cationic surfactants include aminoamide, quaternary ammonium salt, aminoamides (e.g., stearamidopropyl ethyldimonium ethosulfate, stearamidopropyl PG-dimonium chloride phosphate), and quaternary ammonium salts (e.g., cetyl ammonium chloride, lauryl ammonium chloride, and ditallow dimethyl ammonium chloride).

Various combinations of surfactants can be used if desired.

In certain embodiments, the biocide is a cationic biocides such as a quaternary ammonium salts (e.g., dodecyldimethyl benzyl ammonium chloride, tridecyldimethyl benzyl ammonium chloride, tetradecyldimethyl benzyl ammonium chloride, pentadecyldimethyl benzyl ammonium chloride, hexadecyldimethyl benzyl ammonium chloride, (butyl)(dodecyl)dimethyl ammonium chloride, (hexyl)(decyl)dimethyl ammonium chloride, dioctyldimethyl ammonium chloride), polyhexamethyl biguanide (PHMB), and chlorhexidine gluconate), aldehydes (e.g., formaldehyde, glutaraldehyde, parabens), phenolic biocides (e.g., those described in U.S. Pat. No. 6,113,933 (Beerse et al.), including thymol, tricosan, 0-penyl-phenol, p-chlorophenol, benzyl alcohol), essential oils (e.g., oils derived from herbs, flowers, trees, and other plants such as thyme, lemongrass, citrus, lemons, orange, anise, clove, lavender, cedar), metal salts (e.g., aluminum, silver, zinc, copper, and those described in U.S. Pat. No. 6,113,933), and antimicrobial lipids such as a (C8-C12) saturated fatty acid ester of a polyhydric alcohol, a (C12-C22) unsaturated fatty acid ester of a polyhydric alcohol, a (C8-C12) saturated fatty ether of a polyhydric alcohol, a (C12-C22) unsaturated fatty ether of a polyhydric alcohol, an alkoxylated derivative thereof, (C5-C12)1,2-saturated alkanediol, and (C12-C18)1,2-unsaturated alkanediol or combinations thereof (e.g., those described in U.S. Pub. No. 2005/0058673 (Scholz et al.)), peroxy acids (e.g., hydrogen peroxide, peracetic acid), and alcohols (e.g., ethyl alcohol, propyl alcohol).

In certain embodiments, the biocide is a compound capable of destroying or reducing the concentration of bacteria including *Staphylococcus* spp., *Streptococcus* spp., *Escherichia* spp., *Enterococcus* spp., *Pseudamonas* spp., or combinations thereof. In certain embodiments, the biocide is an antibacterial that destroys or reduces the concentration of *Staphylococcus aureus*, *Staphylococcus epidermidis*, *Escherichia coli*, *Pseudomonas aeruginosa*, *Streptococcus pyogenes*, or combinations thereof.

Various combinations of biocides can be used if desired.

Exemplary Embodiments

1. A fiber comprising:
   an aliphatic polyester; and
   an unreacted epoxidized fatty ester having greater than 4.7 wt-% oxirane oxygen, based on the total weight of the epoxidized fatty ester;
   wherein the aliphatic polyester and epoxidized fatty ester form a mixture; and
   wherein the unreacted epoxidized fatty ester is present in an amount of at least 0.5 wt-%, based on the total weight of the mixture.
2. The fiber of embodiment 1 wherein the unreacted epoxidized fatty ester has at least 5.5 wt-% oxirane oxygen.
3. The fiber of embodiment 2 wherein the unreacted epoxidized fatty ester has at least 6 wt-% oxirane oxygen.
4. The fiber of embodiment 3 wherein the unreacted epoxidized fatty ester has at least 9 wt-% oxirane oxygen.
5. The fiber of any of embodiments 1 through 4 wherein the unreacted epoxidized fatty ester has up to 23 wt-% oxirane oxygen.
6. The fiber of any of embodiments 1 through 5 wherein the unreacted epoxidized fatty ester is an epoxidized poly(fatty ester).
7. The fiber of claim 6 wherein the epoxidized poly(fatty ester) is a triglyceride of an epoxidized polyunsaturated fatty acid derived from an unsaturated fatty acid selected from linoleic acid, linoelaidic acid, α-linolenic acid, arachidonic acid, eicosapentaenoic acid, docosahexaenoic acid, and combinations thereof.
8. The fiber of embodiment 6 wherein the epoxidized poly(fatty ester) is an epoxidized vegetable oil.
9. The fiber of embodiment 8 wherein the epoxidized vegetable oil is selected from the group of epoxidized soybean oil, epoxidized cottonseed oil, epoxidized wheat germ oil, epoxidized soya oil, epoxidized corn oil, epoxidized sunflower oil, epoxidized safflower oil, epoxidized hemp oil, epoxidized linseed oil, and combinations thereof.
10. The fiber of embodiment 9 wherein the epoxidized vegetable oil is derived from a vegetable oil having a polyunsaturated value of at least 60 grams per 100 grams total oil.
11. The fiber of any of embodiments 8 through 10 wherein the epoxidized vegetable oil comprises a di-ester, tri-ester, or combinations thereof.
12. The fiber of any of embodiments 1 through 11 wherein the unreacted epoxidized fatty ester is present in the mixture in an amount of up to 20 wt-%, based on the total weight of the mixture.
13. The fiber of embodiment 12 wherein the unreacted epoxidized fatty ester is present in the mixture in an amount of up to 10 wt-%, based on the total weight of the mixture.
14. The fiber of embodiment 13 wherein the unreacted epoxidized fatty ester is present in the mixture in an amount of up to 7 wt-%, based on the total weight of the mixture.
15. The fiber of any of embodiments 1 through 14 wherein the unreacted epoxidized fatty ester is present in the mixture in an amount of at least 1 wt-%, based on the total weight of the mixture.
16. The fiber of any of embodiments 1 through 15 wherein the aliphatic polyester is selected from the group of poly(lactide), poly(glycolide), poly(lactide-co-glycolide), poly(L-lactide-co-trimethylene carbonate), poly(dioxanone), poly(butylene succinate), poly(butylene adipate), poly(ethylene adipate), polyhydroxybutyrate, polyhydroxyvalerate, and blends and copolymers thereof.
17. The fiber of embodiment 16 wherein the aliphatic polyester is a poly(lactide).
18. The fiber of any of embodiments 1 through 17 wherein the aliphatic polyester has a number average molecular weight of at least 8,000 Daltons.
19. The fiber of embodiment 18 wherein the aliphatic polyester has a number average molecular weight of at least 10,000 Daltons.
20. The fiber of any of embodiments 18 or 19 wherein the aliphatic polyester has a number average molecular weight of up to 1,000,000 Daltons.

21. The fiber of any of embodiments 1 through 20 wherein the aliphatic polyester is present in an amount of at least 80 wt-%, based on the total weight of the mixture.
22. The fiber of any of embodiments 1 through 21 wherein the mixture further comprises a shrink reduction additive.
23. The fiber of embodiment 22 wherein the shrink reduction additive is a polyolefin.
24. The fiber of embodiment 23 wherein the shrink reduction additive is selected from polyethylene, linear low density polyethylene, polypropylene, polyoxymethylene, poly(vinylidine fluoride), poly(methyl pentene), poly(ethylenechlorotrifluoroethylene), poly(vinyl fluoride), poly(ethylene oxide), poly(ethylene terephthalate), poly(butylene terephthalate), semicrystalline aliphatic polyesters including polycaprolactone, aliphatic polyamides such as nylon 6 and nylon 66, and thermotropic liquid crystal polymers, and combinations thereof. Preferably, the shrink reduction additive is a polypropylene.
25. A web comprising a plurality of the fibers of any of embodiments 1 through 24.
26. The web of embodiment 25 which is a nonwoven web.
27. A wet wipe comprising:
    a nonwoven web of embodiment 26; and
    an aqueous composition comprising water and a surfactant and/or a biocide (dissolved or dispersed in the water), wherein the aqueous composition contacts the nonwoven web.
28. A wet wipe comprising:
    a fibrous web comprising fibers comprising:
        an aliphatic polyester; and
        an unreacted epoxidized fatty ester having greater than 4.7 wt-% oxirane oxygen, based on the total weight of the epoxidized fatty ester;
        wherein the aliphatic polyester and epoxidized fatty ester form a mixture; and
        wherein the unreacted epoxidized fatty ester is present in an amount of at least 0.5 wt-%, based on the total weight of the mixture; and
    an aqueous composition contacting the fibrous web, the aqueous composition comprising:
        water; and
        a surfactant and/or a biocide (dissolved or dispersed in the water).
29. The wet wipe of embodiment 27 or 28 wherein the aqueous composition has a pH of 1 to 14.
30. The wet wipe of any of embodiments 27 through 29 wherein the aqueous composition comprises at least 0.01 wt-% surfactant and/or biocide, based on the total weight of the aqueous composition.
31. The wet wipe of any of embodiments 27 through 30 wherein the aqueous composition comprises a surfactant, wherein the wet wipe is a cleaning wipe.
32. The wet wipe of embodiment 31 wherein the surfactant comprises a nonionic surfactant.
33. The wet wipe of any of embodiments 27 through 30 wherein the aqueous composition comprises a biocide, wherein the wet wipe is a disinfecting wipe.
34. The wet wipe of any of embodiments 27 through 30 wherein the aqueous composition comprises a biocide and a surfactant, wherein the wet wipe is a cleaning/disinfecting wipe.
35. The wet wipe of any of embodiments 27 through 34 wherein the aqueous composition is present in an amount of at least 2 times the weight of the fibrous web.
36. A process for improving the hydrolytic stability of fibers comprising an aliphatic polyester, the method comprising:
    mixing components comprising an aliphatic polyester, an epoxidized fatty ester, and an optional shrink reduction additive to form a mixture;
        wherein the unreacted epoxidized fatty ester has at least 4.7 wt-% oxirane oxygen, based on the total weight of the epoxidized fatty ester; and
        wherein the unreacted epoxidized fatty ester is present in an amount of at least 0.5 wt-%, based on the total weight of the mixture; and
    forming fibers out of the mixture.
37. The process of embodiment 36 wherein forming fibers out of the mixture comprises forming spunbond fibers.

EXAMPLES

Objects and advantages of this invention are further illustrated by the following examples, but the particular materials and amounts thereof recited in these examples, as well as other conditions and details, should not be construed to unduly limit this invention. These examples are merely for illustrative purposes only and are not meant to be limiting on the scope of the appended claims.

Materials

NATUREWORKS PLA Polymer 6202D, (PLA), poly(lactic acid), available from NatureWorks LLC, Minnetonka, Minn.

Polypropylene 3860X, (PP), polypropylene homopolymer (melt index=100 grams/10 minutes) available from Total Petrochemicals, Houston, Tex.

PARAPLEX G-60, (G-60), epoxidized soybean oil with 5.5 wt-% of oxirane oxygen, available from The HallStar Company, Chicago, Ill.

STEROTEX NF, hydrogenated cottonseed oil with 0 wt-% oxirane oxygen (CAS No. 68334-00-9), available from Abitec, Columbus, Ohio VIKOFLEX 7170, (VK-7170), epoxidized soybean oil with a minimum oxirane oxygen content of 7.0 wt-%, available from Arkema Inc., King of Prussia, Pa.

VIKOFLEX 7190, (VK-7190), epoxidized linseed oil with a minimum oxirane oxygen content of 9.0 wt-%, available from Arkema Inc., King of Prussia, Pa.

Preparation of Compounded Pellets of PLA with Additives

Compounded pellets of PLA with additives such as epoxidized vegetable oils were produced using a 40 mm twin-screw extruder (Berstorff Ultra Glide laboratory extruder available from KraussMaffei Berstorff GmbH, Germany) by mixing pre-dried PLA 6202D resin with the additive at a melt temperature of 371° F. (188° C.) and then extruding at a rate of 60 lb/hour (27 kg/hour). The pre-drying of the PLA resin was accomplished in a Conair dryer with 130° F. (55° C.) hot air at the flow rate of 45-55 CFM (1275-1550 liters per minute) and dew point of −34° F. (−37° C.) for 15 hours. The compounded material was quenched in a water bath and pelletized using a Conair Model 304 Pelletizer available from Conair USA, Franklin, Pa. The pellets were then immediately dried overnight in a Conair dryer at 170° F. (77° C.) with a dry air flow rate of 45-55 CFM (1275-1550 liters per minute) and dew point of −34° F. (−37° C.).

PLA Spunbond Nonwoven Web Preparation

PLA spunbond nonwoven webs according to the Examples and Comparative Examples described below were made from PLA pellets and the compounded PLA/additive pellets prepared as described above. The PLA spunbond nonwoven webs were generally prepared on an experimental spunbond line using the equipment and processing techniques for spunbond nonwoven webs described in U.S. Patent Publication 2008/0038976 (Berrigan et al.).

In a typical procedure, the PLA pellets or the PLA/additive pellets prepared above were fed from a hopper into a 2 inch (5.1 cm) single screw extruder (Davis-Standard BLUE RIBBON (DS-20®) available from Davis Standard Corporation, Pawcatuck, Conn.) at controlled rate for a designed ratio. The extruder temperature was 230° C. The molten resin was pumped via a gear pump into a spin pack having rows of small orifices. The orifices, arranged in a rectangular form, had a diameter of 0.014 inch (0.36 mm) and a length to diameter ratio (L/D) of 4. Fibers were formed through the spin pack and subsequently cooled down by passing them through a quenching air chamber. The rate and extent of fiber attenuation was controlled by the attenuating pressure (AP) of the attenuator air—the higher the attenuating pressure, the faster and greater the extent of attenuation. The attenuated PLA fibers were collected as an unbonded fiber mat on a conventional screen support using vacuum assistance, and the fiber mat was then passed through a through-air bonder at a temperature of 147° C. in order to cause light autogeneous bonding between at least some of the fibers. The web was subsequently treated by a typical hydroentangling/spunlacing process and then dried. This further bonded the fibers in the web and provided web softness.

Preparation of Spunbond Nonwoven Webs with Poly(b-hydroxybutyrate-co-hydroxyvalerate) (PHBV), and PHBV with Additives Poly(b-hydroxybutyrate-co-hydroxyvalerate) (PHBV) power is commercially available (e.g., Zhejiang Biological Materials Company). PHBV powder with additives such as epoxidized vegetable oil (EVO), including for example epoxidized soybean oil, and polypropylene (PP), can be produced using a 40 mm twin-screw extruder (Berstorff Ultra Glide laboratory extruder available from KraussMaffei Berstorff GmbH, Germany) by mixing pre-dried PLA resin with the additive at a melt temperature of 180° C. and then extruding at a rate of 60 lb/hour (27 kg/hour). The PHBV is pre-dried before compounding. The compounded material is quenched in a water bath and pelletized using a pelletizer such as Conair Model 304 Pelletizer available from Conair USA, Franklin, Pa. The pellets are then immediately dried overnight in a Conair dryer.

The PHBV spunbond nonwoven webs are prepared on an experimental spunbond line using the equipment and processing techniques for spunbond nonwoven webs described in U.S. Patent Publication No. 2008/0038976. Typically, the PHBV pellets prepared above are fed from a hopper into a 2 inch (5 cm) single screw extruder (Davis-Standard BLUE RIBBON (DS-20) available from Davis Standard Corporation, Pawcatuck, Conn.). The extruder temperature is 230° C. The molten resin is pumped via a gear pump into a spin pack having rows of small orifices. The orifices, arranged in a rectangular form, have a diameter of 0.014 inch (0.36 mm) and a length to diameter ratio (L/D) of 4. Fibers are formed through the spin pack and subsequently cooled down by passing them through a quenching air chamber. The rate and extent of fiber attenuation is controlled by the attenuating pressure (AP) of the attenuator air—the higher the attenuating pressure, the faster and greater the extent of attenuation. The attenuated PLA fibers are collected as an unbonded fiber mat on a conventional screen support using vacuum assistance, and the fiber mat then passes through a through-air bonder (TAB) at a temperature of 147° C. in order to cause light autogeneous bonding between at least some of the fibers. The web is subsequently treated by a typical hydroentangling/spunlacing process and then dried. This further bonds the fibers in the web and provides web softness.

Method for Preparing Wet Wipes Using the PLA Spunbond Nonwoven Webs for Aging Studies The aging stability of PLA spunbond nonwoven webs was studied in three different water based cleaning/disinfecting solutions:

Solution 1 (S1):

an aqueous cleaning solution comprising 1 wt-% GLUCOPON 425N alkyl polyglycoside surfactant (available from BASF Chemical Company, Florham Park, N.J.), 0.02 wt-% EASY WET 20 wetting agent (based on N-Octyl-2-Pyrrolidone, available from Ashland Inc., Covington, Ky.), 0.01 wt-% DOW CORNING 7305 silicone based antifoam emulsion (available from Dow Corning Corporation, Midland, Mich.) 0.2 wt-% MACKSTAT DM 55% active solution of Dimethylol-5,5-dimethylhydantoin (available from Rhodia, Cranbury, N.J.), 0.03 wt-% OMACIDE IPBC 30 DPG fungicide (based on 3-Iodopropynylbutylcarbamate, available from Arch Chemicals, Atlanta, Ga.), 0.15 wt-% fragrance (No. 70331 citrus fragrance, available from Belle-Aire Fragrances, Mundelein, Ill.), and 98.59 wt-% water. The pH of this solution was 7.0.

Solution 2 (S2):

an aqueous solution of Lonza LC-75, a quaternary ammonium compound based aqueous disinfectant solution (EPA Registration Number: 6836-334), available from Lonza Inc., Allendale, N.J. The Lonza LC-75 was diluted 1:75 with water to prepare Solution 2. The pH of this solution was 10.5.

Solution 3 (S3):

an aqueous disinfectant solution comprising 0.24 wt % CAPMUL 908P Propylene glycol monocaprylate (available from Abitec Corporation, Columbus, Ohio), 0.3 wt-% Citric acid (available from Sigma Aldrich, St. Louis, Mo.), 0.3 wt-% Sorbic acid (available from Sigma Aldrich, St. Louis, Mo.), 0.81 wt-% Propylene glycol (available from Dow Chemical Company, Midland, Mich.), 0.49 wt-% NAXOLATE AS-LG-85 Sodium Lauryl Sulfate (available from Nease Corporation, Blue Ash, Ohio), 0.13 wt-% Sodium hydroxide (20% solution, available from Sigma Aldrich, St. Louis, Mo.), and 97.73 wt-% water. The pH of this solution was 4.5.

The PLA spunbond nonwoven webs were cut into 6 inch×5 inch (15.2 cm×12.7 cm) samples, and an excess of the cleaning/disinfecting solution used for testing was loaded onto the webs (generally about 5-6 times the web weight). The wipes were then sealed in an aluminum bag and aged in an oven maintained at a temperature of either 135° F. or 158° F. (57° C. or 70° C.) over a period of time as indicated in the Examples. After removing the webs from the oven, excess cleaning solution was squeezed from the webs by passing the webs between nip rollers. The hydrolytic stability of the PLA spunbond nonwoven web with epoxidized vegetable oils additive in comparison to the untreated PLA spunbond nonwoven webs was then assessed by measuring the tensile strength and the % tensile strength retention of the webs.

Test Method for Tensile Strength and % Retention

Tensile strength measurements were carried out using a Lloyd LF Plus tensile tester (available from Lloyd Instruments, Segensworth Fareham England). The size of the nonwoven web samples that were tested was 1 inch (2.54 cm)×3 inch (7.6 cm) (width×length), and the gap for the tensile measurement was ⅛ inch (0.32 cm). Measurements were in the machine direction (length direction of the test sample) unless indicated otherwise, at a rate of 14 inches per minute. The tensile strength in this experiment is defined as the maximum load when the nonwoven web is broken with 1 kg load, and is the average measurement of 8 replicate nonwoven web samples. The % tensile strength retention (i.e., % retention) was calculated by dividing the tensile strength after aging by the initial tensile strength and multiplying by 100.

Method for Determining Epoxy Equivalent Weight (EEW) and % Oxirane Oxygen Content The epoxy equivalent weight of the samples was measured and calculated using titrimetry according to the following procedure. Each sample (about 0.5-0.9 milliequivalents epoxy) was weighed to the nearest 0.0001 gram and was then dissolved in 50 mL chloroform in a 100 mL beaker and stirred magnetically until dissolved. A solution of 10 weight percent tetrabutylammonium iodide in acetic acid (10 mL) and acetic acid (20 mL) was added to the sample solution and stirred for approximately 15 minutes. A drop of 0.1 weight percent methyl violet indicator solution in acetic acid was then added. The mixture was titrated with a 0.1 N solution of perchloric acid in acetic acid to the potentiometric endpoint. The potentiometer was a Metrohm 751 Titrino with a Metrohm 6.0229.010 Solvotrode electrode that was obtained from Metrom AG, Switzerland. A blank was titrated using the sample procedure without the sample aliquot. The volume for the blank titration was subtracted from the total titration volume from the above procedure. Samples were run in triplicate.

Calculations were performed as shown below:

% Epoxy containing compound=[100(V)(N)(Eq. Wt.)]÷[1000(SW)]

Epoxy Equivalent Weight (EEW)=[1000(SW)]÷[(V)(N)]

% oxirane content=[100×(V)×(N)×16]÷[1000(SW)]

where V is the Volume of titrant used in milliliters, N is the Normality of the titrant, SW is the Sample Weight in grams, and Eq. Wt. is the Equivalent Weight. The Equivalent Weight is the Molecular Weight of the epoxy containing compound in grams divided by the number of equivalents per gram.

Examples 1-6 and Comparative Examples C1 and C2

PLA spunbond nonwoven webs that included different amounts of PARAPLEX G-60 epoxidized soybean oil additive were prepared using the methods described above (AP was 12 psi). The dry basis weight of the webs was about 60 grams/meter$^2$. Wet wipes were prepared using Solution 1 (S1). The wet wipes were aged at 135° F. and 158° F. (57° C. or 70° C.) and tensile strength data was obtained as described above. PLA spunbond nonwoven webs with hydrogenated cottonseed oil as the additive were similarly prepared and tested as Comparative Examples. Control data for a PLA spunbond nonwoven web sample without any additive is also included in the Tables for comparison. The PLA spunbond nonwoven web compositions, tensile strength, and % retention data are provided in Tables 1-4.

TABLE 1

Tensile Strength (kgf) - 135° F. (57° C.) aging

| | | Example | | | |
|---|---|---|---|---|---|
| Aging (days) | Control 1 PLA | C1 PLA/ STEROTEX (99:1) | 1 PLA/G-60 (99:1) | 2 PLA/G-60 (97.5:2.5) | 3 PLA/G-60 (95:5) |
| 0 | 8.2331 | 11.2745 | 8.8178 | 9.4199 | 7.0998 |
| 8 | 5.5468 | 7.0834 | 5.6777 | 4.976 | 4.4179 |
| 14 | 6.4216 | 7.0777 | 6.9265 | 6.7929 | 6.2217 |
| 22 | 4.6507 | 5.2732 | 5.9683 | 4.8838 | 4.4071 |
| 27 | 2.8418 | 3.6124 | 5.0892 | 4.0796 | 4.1873 |
| 29 | 1.9688 | 2.0871 | 4.1232 | 2.862 | 4.5447 |
| 31 | 1.3527 | 1.409 | 3.1741 | 2.5956 | 3.7585 |
| 33 | 0.8745 | 0.7697 | 2.8646 | 2.0837 | 3.5784 |
| 35 | 0.2322 | 0.2221 | 2.0093 | 1.1335 | 3.0139 |
| 37 | 0 | 0 | 1.1643 | 1.1476 | 2.5453 |

TABLE 2

% Retention - 135° F. (57° C.) aging

| | | Example | | | |
|---|---|---|---|---|---|
| Aging (days) | Control 1 PLA | C1 PLA/ STEROTEX (99:1) | 1 PLA/G-60 (99:1) | 2 PLA/G-60 (97.5:2.5) | 3 PLA/G-60 (95:5) |
| 0 | 100 | 100 | 100 | 100 | 100 |
| 8 | 67 | 63 | 64 | 53 | 62 |
| 14 | 78 | 63 | 79 | 72 | 88 |
| 22 | 56 | 47 | 68 | 52 | 62 |
| 27 | 35 | 32 | 58 | 43 | 59 |
| 29 | 24 | 19 | 47 | 30 | 64 |
| 31 | 16 | 12 | 36 | 28 | 53 |
| 33 | 11 | 7 | 32 | 22 | 50 |
| 35 | 3 | 2 | 23 | 12 | 42 |
| 37 | 0 | 0 | 13 | 12 | 36 |

TABLE 3

Tensile Strength (kgf) - 158° F. (70° C.) aging

| | | Example | | | |
|---|---|---|---|---|---|
| Aging (days) | Control 1 PLA | C2 PLA/ STEROTEX (99:1) | 4 PLA/G-60 (99:1) | 5 PLA/G-60 (97.5:2.5) | 6 PLA/G-60 (95:5) |
| 0 | 8.2331 | 11.2745 | 8.8178 | 9.4199 | 7.0998 |
| 1 | 6.8185 | 7.5194 | 7.0286 | 7.9318 | 6.2714 |
| 2 | 6.5168 | 7.7490 | 7.0710 | 7.0381 | 5.8508 |
| 3 | 6.1411 | 7.7817 | 6.7535 | 5.7406 | 5.6909 |
| 4 | 5.2758 | 5.4731 | 6.5269 | 4.9829 | 5.4677 |
| 5 | 3.9583 | 3.8225 | 5.4617 | 4.0798 | 4.8829 |
| 6 | 1.9964 | 1.9671 | 3.4406 | 1.7643 | 3.5170 |
| 7 | 0.3093 | 0 | 1.5397 | 0.9959 | 2.0981 |
| 8 | 0 | | 0.4048 | 0.4145 | 1.5740 |

TABLE 4

% Retention - 158° F. (70° C.) aging

| Aging (days) | Control 1 PLA | C2 PLA/ STEROTEX (99:1) | Example 4 PLA/G-60 (99:1) | 5 PLA/G-60 (97.5:2.5) | 6 PLA/G-60 (95:5) |
|---|---|---|---|---|---|
| 0 | 100 | 100 | 100 | 100 | 100 |
| 1 | 83 | 67 | 80 | 84 | 88 |
| 2 | 79 | 69 | 80 | 75 | 82 |
| 3 | 75 | 69 | 77 | 61 | 80 |
| 4 | 64 | 49 | 74 | 53 | 77 |
| 5 | 48 | 34 | 62 | 43 | 69 |
| 6 | 24 | 17 | 39 | 19 | 50 |
| 7 | 4 | 0 | 17 | 11 | 30 |
| 8 | 0 |   | 5 | 4 | 22 |

Examples 7-10

PLA spunbond nonwoven webs and wet wipes were prepared and tested as described above for Examples 1-6 except the epoxidized vegetable oil additives had a higher minimum wt-% oxirane oxygen content (7.0% and 9.0%). The PLA spunbond nonwoven web compositions, tensile strength, and % retention data for Examples 7-10 are provided in Tables 5-8. The tensile strength data for a control PLA spunbond nonwoven web sample without any additive and the tensile strength data for Examples 3 and 6 (5.5 wt-% oxirane oxygen) are also included in the Tables for comparison.

TABLE 5

Tensile Strength (kgf) - 135° F. (57° C.) aging

| Aging (days) | Control 1 PLA | Example 3 PLA/G-60 (95:5) | 7 PLA/VK-7170 (95:5) | 8 PLA/VK-7190 (95:5) |
|---|---|---|---|---|
| 0 | 8.2331 | 7.0998 | 9.7044 | 9.1883 |
| 8 | 5.5468 | 4.4179 | 5.7111 | 6.2569 |
| 14 | 6.4216 | 6.2217 | 7.7305 | 7.5209 |
| 22 | 4.6507 | 4.4071 | 6.1349 | 6.2414 |
| 27 | 2.8418 | 4.1873 | 6.5289 | 7.0018 |
| 29 | 1.9688 | 4.5447 | 5.8967 | 6.7105 |
| 31 | 1.3527 | 3.7585 | 5.3636 | 6.5718 |
| 33 | 0.8745 | 3.5784 | 5.6155 | 6.2926 |
| 35 | 0.2322 | 3.0139 | 4.585 | 5.6353 |
| 37 | 0 | 2.5453 | 4.8547 | 6.3735 |

TABLE 6

% Retention - 135° F. (57° C.) aging

| Aging (days) | Control 1 PLA | Example 3 PLA/G-60 (95:5) | 7 PLA/VK-7170 (95:5) | 8 PLA/VK-7190 (95:5) |
|---|---|---|---|---|
| 0 | 100 | 100 | 100 | 100 |
| 8 | 67 | 62 | 59 | 68 |
| 14 | 78 | 88 | 80 | 82 |
| 22 | 56 | 62 | 63 | 68 |
| 27 | 35 | 59 | 67 | 76 |

TABLE 6-continued

% Retention - 135° F. (57° C.) aging

| Aging (days) | Control 1 PLA | Example 3 PLA/G-60 (95:5) | 7 PLA/VK-7170 (95:5) | 8 PLA/VK-7190 (95:5) |
|---|---|---|---|---|
| 29 | 24 | 64 | 61 | 73 |
| 31 | 16 | 53 | 55 | 72 |
| 33 | 11 | 50 | 58 | 68 |
| 35 | 3 | 42 | 47 | 61 |
| 37 | 0 | 36 | 50 | 69 |

TABLE 7

Tensile Strength (kgf) - 158° F. (70° C.) aging

| Aging (days) | Control 1 PLA | Example 6 PLA/G-60 (95:5) | 9 PLA/VK-7170 (95:5) | 10 PLA/VK-7190 (95:5) |
|---|---|---|---|---|
| 0 | 8.2331 | 7.0998 | 9.7044 | 9.1883 |
| 1 | 6.8185 | 6.2714 | 8.0252 | 7.6913 |
| 2 | 6.5168 | 5.8508 | 7.7284 | 7.7978 |
| 3 | 6.1411 | 5.6909 | 6.1731 | 7.5299 |
| 4 | 5.2758 | 5.4677 | 6.4471 | 6.5388 |
| 5 | 3.9583 | 4.8829 | 5.0749 | 5.4572 |
| 6 | 1.9964 | 3.5170 | 3.9304 | 6.1711 |
| 7 | 0.3093 | 2.0981 | 2.5223 | 4.5418 |
| 8 | 0 | 1.5740 | 1.5692 | 3.9213 |

TABLE 8

% Retention - 158° F. (70° C.) aging

| Aging (days) | Control 1 PLA | Example 6 PLA/G-60 (95:5) | 9 PLA/ VK-7170 (95:5) | 10 PLA/ VK-7190 (95:5) |
|---|---|---|---|---|
| 0 | 100 | 100 | 100 | 100 |
| 1 | 83 | 88 | 83 | 84 |
| 2 | 79 | 82 | 80 | 85 |
| 3 | 75 | 80 | 64 | 82 |
| 4 | 64 | 77 | 66 | 71 |
| 5 | 48 | 69 | 52 | 59 |
| 6 | 24 | 50 | 41 | 67 |
| 7 | 4 | 30 | 26 | 49 |
| 8 | 0 | 22 | 16 | 43 |

Examples 11-15 and Comparative Example C3

PLA spunbond nonwoven webs with epoxidized vegetable oil additives and PLA spunbond nonwoven webs with a hydrogenated cottonseed oil additive were prepared and tested as described for the examples above, except that Solution 2 (S2) was used to prepare the wet wipes and the samples were only aged at 158° F. (70° C.). The PLA spunbond nonwoven web compositions, tensile strength, and % retention data are provided in Tables 9 and 10. Control data for a PLA spunbond nonwoven web sample without any additive is also included in the Tables for comparison.

TABLE 9

Tensile Strength (kgf)-158° F. (70° C.) aging

| Aging (days) | Control 2 PLA | C3 PLA/ STEROTEX (99:1) | 11 PLA/ G-60 (99:1) | 12 PLA/ G-60 (97.5:2.5) | 13 PLA/ G-60 (95:5) | 14 PLA/ VK-7170 (95:5) | 15 PLA/ VK-7190 (95:5) |
|---|---|---|---|---|---|---|---|
| 0 | 8.1650 | 9.3456 | 9.1263 | 9.6192 | 7.5406 | 10.6996 | 9.5319 |
| 1 | 7.2035 | 9.4574 | 6.7291 | 8.1437 | 5.7979 | 8.3712 | 8.2149 |
| 2 | 6.2132 | 7.5551 | 6.2616 | 6.0255 | 4.9008 | 7.3545 | 7.2061 |
| 3 | 3.5920 | 4.3875 | 4.8195 | 3.5594 | 3.4573 | 5.8772 | 6.4496 |
| 4 | 1.7399 | 1.5399 | 2.0234 | 1.3148 | 1.7868 | 3.4993 | 5.4484 |
| 5 | 0.7926 | 0.8746 | 0.6919 | 0.3833 | 0.8505 | 2.0875 | 5.0001 |
| 6 | 0.2434 | 0.2047 | 0 | 0 | 0 | 0.2793 | 4.3053 |
| 7 |  | 0 |  |  |  | 0 | 2.6215 |
| 8 |  |  |  |  |  |  | 1.6567 |

TABLE 10

% Retention-158° F. (70° C.) aging

| Aging (days) | Control 2 PLA | C3 PLA/ STEROTEX (99:1) | 11 PLA/ G-60 (99:1) | 12 PLA/ G-60 (97.5:2.5) | 13 PLA/ G-60 (95:5) | 14 PLA/ VK-7170 (95:5) | 15 PLA/ VK-7190 (95:5) |
|---|---|---|---|---|---|---|---|
| 0 | 100 | 100 | 100 | 100 | 100 | 100 | 100 |
| 1 | 88 | 101 | 74 | 85 | 77 | 78 | 86 |
| 2 | 76 | 81 | 69 | 63 | 65 | 69 | 76 |
| 3 | 44 | 47 | 53 | 37 | 46 | 55 | 68 |
| 4 | 21 | 16 | 22 | 14 | 24 | 33 | 57 |
| 5 | 10 | 9 | 8 | 4 | 11 | 20 | 52 |
| 6 | 3 | 2 | 0 | 0 | 0 | 3 | 45 |
| 7 |  |  |  |  |  | 0 | 28 |
| 8 |  |  |  |  |  |  | 17 |

Examples 16-20 and Comparative Example C4

PLA spunbond nonwoven webs with epoxidized vegetable oil additives and PLA spunbond nonwoven webs with a hydrogenated cottonseed oil additive were prepared and tested as described above for Examples 11-15 and Comparative Example C3, except the wet wipes were prepared using Solution 3 (S3). The PLA spunbond nonwoven web compositions, tensile strength, and % retention data are provided in Tables 11 and 12. Control data for a PLA spunbond nonwoven web sample without any additive is also included in the Tables for comparison.

TABLE 11

Tensile Strength (kgf)-158° F. (70° C.) aging

| Aging (days) | Control 3 PLA | C4 PLA/ STEROTEX (99:1) | 16 PLA/ G-60 (99:1) | 17 PLA/ G-60 (97.5:2.5) | 18 PLA/ G-60 (95:5) | 19 PLA/ VK-7170 (95:5) | 20 PLA/ VK-7190 (95:5) |
|---|---|---|---|---|---|---|---|
| 0 | 7.6367 | 10.3987 | 8.6853 | 9.3095 | 6.8746 | 9.4467 | 8.8587 |
| 1 | 5.6313 | 6.2917 | 6.4398 | 4.8851 | 4.6559 | 6.2299 | 6.4630 |
| 2 | 3.2372 | 4.3848 | 4.3056 | 2.8435 | 3.0478 | 5.0349 | 5.1382 |
| 3 | 0.991 | 0.4582 | 1.5940 | 0.8559 | 1.2322 | 2.1050 | 3.0362 |
| 4 | 0 | 0 | 0 | 0 | 0 | 0.4035 | 0.7673 |
| 5 |  |  |  |  |  |  | 0.2890 |

TABLE 12

% Retention-158° F. (70° C.) aging

| Aging (days) | Control 3 PLA | C4 PLA/ STEROTEX (99:1) | 16 PLA/ G-60 (99:1) | 17 PLA/ G-60 (97.5:2.5) | 18 PLA/ G-60 (95:5) | 19 PLA/ VK-7170 (95:5) | 20 PLA/ VK-7190 (95:5) |
|---|---|---|---|---|---|---|---|
| 0 | 100 | 100 | 100 | 100 | 100 | 100 | 100 |
| 1 | 74 | 61 | 74 | 52 | 68 | 66 | 73 |
| 2 | 42 | 42 | 50 | 31 | 44 | 53 | 58 |
| 3 | 13 | 4 | 18 | 9 | 18 | 22 | 34 |
| 4 | 0 | 0 | 0 | 0 | 0 | 4 | 9 |
| 5 | | | | | | | 3 |

Examples 21 and 22

PLA spunbond nonwoven webs that included a polypropylene anti-shrinkage additive in addition to an epoxidized soybean oil additive were prepared using the methods described above (AP was 9 psi). The dry basis weight of the webs was about 60 grams/meter². Wet wipe samples were prepared using Solution 1 (S1) and were aged at 135° F. and 158° F. (57° C. or 70° C.). The PLA spunbond nonwoven web compositions, tensile strength, and % retention data are provided in Tables 13 and 14. Control data for a PLA spunbond nonwoven web sample without any epoxidized soybean oil additive and control data control for a PLA spunbond nonwoven web sample having only the polypropylene shrink additive are also included in the Tables for comparison.

TABLE 13

Tensile Strength (kgf) and % Retention-135° F. (57° C.) aging

| | Example | | | | | |
|---|---|---|---|---|---|---|
| | Control 4 PLA | | Control 5 PLA/PP (98:2) | | 21 PLA/PP/G-60 (95:2:3) | |
| Aging (days) | Tensile Strength | % Retention | Tensile Strength | % Retention | Tensile Strength | % Retention |
| 0 | 6.9205 | 100 | 8.2054 | 100 | 7.0737 | 100 |
| 8 | 5.0113 | 72 | 5.1284 | 63 | 4.0916 | 58 |
| 14 | 6.2121 | 90 | 7.0850 | 86 | 5.9883 | 85 |
| 22 | 4.6225 | 67 | 5.0108 | 61 | 3.7744 | 53 |
| 27 | 3.5430 | 51 | 3.7402 | 46 | 4.2276 | 60 |
| 29 | 2.6394 | 38 | 2.7509 | 34 | 3.5182 | 50 |
| 31 | 1.6919 | 24 | 1.9602 | 24 | 3.6775 | 52 |
| 33 | 0.9465 | 14 | 1.2028 | 15 | 3.1348 | 44 |
| 35 | 0.3918 | 6 | 0.5746 | 7 | 2.0762 | 29 |
| 37 | | | | | 2.2730 | 32 |

TABLE 14

Tensile Strength (kgf) and % Retention-158° F. (70° C.) aging

| | Example | | | | | |
|---|---|---|---|---|---|---|
| | Control 4 PLA | | Control 5 PLA/PP (98:2) | | 22 PLA/PP/G-60 (95:2:3) | |
| Aging (days) | Tensile Strength | % Retention | Tensile Strength | % Retention | Tensile Strength | % Retention |
| 0 | 6.920 | 100 | 8.205 | 100 | 7.074 | 100 |
| 1 | 6.661 | 96 | 7.025 | 86 | 5.693 | 80 |
| 2 | 5.740 | 83 | 7.114 | 87 | 6.261 | 89 |
| 3 | 5.647 | 82 | 5.861 | 71 | 5.923 | 84 |
| 4 | 4.922 | 71 | 5.172 | 63 | 4.156 | 59 |
| 5 | 3.952 | 57 | 4.510 | 55 | 3.888 | 55 |
| 6 | 1.922 | 28 | 2.741 | 33 | 2.834 | 40 |
| 7 | 0.437 | 6 | 0.737 | 9 | 1.949 | 28 |
| 8 | | | | | 0.485 | 7 |

Example 23

PLA spunbond web samples that included a polypropylene anti-shrinkage additive in addition to an epoxidized soybean oil additive were prepared using the methods described above (AP was 12 psi). The dry basis weight of the webs was about 60 grams/meter$^2$. Wet wipes were prepared using Solution 3 (S3) and were aged at 158° F. (70° C.). The PLA spunbond nonwoven web compositions, tensile strength, and % retention data are provided in Table 15. Control data for a PLA spunbond nonwoven web sample without any epoxidized soybean oil additive are also included in the Table for comparison.

TABLE 15

Tensile Strength (kgf) and % Retention - 158° F. (70° C.) aging

| | Example | | | |
|---|---|---|---|---|
| | Control 6 PLA | | 23 PLA/PP/G-60 (95:2:3) | |
| Aging (days) | Tensile Strength | % Retention | Tensile Strength | % Retention |
| 0 | 7.6367 | 100 | 7.0444 | 100 |
| 1 | 5.6313 | 74 | 5.3047 | 75 |
| 2 | 3.2372 | 42 | 3.8243 | 54 |
| 3 | 0.991 | 13 | 1.2373 | 18 |
| 4 | 0 | 0 | 0 | 0 |

Generally, the data presented in Tables 1-15 for exemplary fibrous webs of the present disclosure show improvement (e.g., by greater than 10% increase) in tensile strength after aging at a temperature of 135° F. for at least 25 days (in one of the three aqueous cleaning and/or disinfecting solutions), compared to a web made of fibers of the same aliphatic polyester without the exemplified epoxidized fatty esters. Although there are certain data points for some examples (Example 2) that appear to be anomalies, and some samples show contrary results at a higher aging temperature (158° F.) (Examples 11-13 and 17), it is believed that there is a general trend of improvement demonstrated by these examples with the use of epoxidized fatty esters.

The complete disclosures of the patents, patent documents, and publications cited herein are incorporated by reference in their entirety as if each were individually incorporated. Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed is:

1. A wet wipe comprising:
a nonwoven web comprising a plurality of fibers, wherein each fiber comprises:
an aliphatic polyester having a number average molecular weight of at least 8,000 Daltons; and
an unreacted epoxidized fatty ester having greater than 4.7 wt-% oxirane oxygen, based on the total weight of the epoxidized fatty ester;
wherein the aliphatic polyester and epoxidized fatty ester form a mixture; and
wherein the unreacted epoxidized fatty ester is present in an amount of at least 0.5 wt-%, based on the total weight of the mixture; and
wherein the epoxidized fatty ester is selected to provide a nonwoven web that demonstrates greater tensile strength after aging at a temperature of 135° F. for at least 25 days in an aqueous cleaning and/or disinfecting solution, compared to a nonwoven web made of fibers of the same aliphatic polyester without the epoxidized fatty ester, to an extent of greater than 10%; and
an aqueous composition comprising water and a surfactant and/or a biocide, wherein the aqueous composition contacts the nonwoven web.

2. The wet wipe of claim 1 wherein the unreacted epoxidized fatty ester has at least 5.5 wt-% oxirane oxygen.

3. The wet wipe of claim 1 wherein the unreacted epoxidized fatty ester has up to 23 wt-% oxirane oxygen.

4. The wet wipe of claim 1 wherein the unreacted epoxidized fatty ester is an epoxidized poly(fatty ester).

5. The wet wipe of claim 1 wherein the unreacted epoxidized fatty ester is present in the mixture in an amount of up to 20 wt-%, based on the total weight of the mixture.

6. The wet wipe of claim 1 wherein the unreacted epoxidized fatty ester is present in the mixture in an amount of at least 1 wt-%, based on the total weight of the mixture.

7. The wet wipe of claim 1 wherein the aliphatic polyester is selected from the group of poly(lactide), poly(glycolide), poly(lactide-co-glycolide), poly(L-lactide-co-trimethylene carbonate), poly(dioxanone), poly(butylene succinate), poly(butylene adipate), poly(ethylene adipate), polyhydroxybutyrate, polyhydroxyvalerate, and blends and copolymers thereof.

8. The wet wipe of claim 7 wherein the aliphatic polyester is a poly(lactide).

9. The wet wipe of claim 1 wherein the aliphatic polyester is present in an amount of at least 80 wt-%, based on the total weight of the mixture.

10. The wet wipe of claim 1 wherein the mixture further comprises a shrink reduction additive.

11. The wet wipe of claim 10 wherein the shrink reduction additive is a polyolefin.

12. A wet wipe comprising:
a fibrous web comprising fibers comprising:
an aliphatic polyester having a number average molecular weight of at least 8,000 Daltons; and
an unreacted epoxidized fatty ester having greater than 4.7 wt-% oxirane oxygen, based on the total weight of the epoxidized fatty ester;
wherein the aliphatic polyester and epoxidized fatty ester form a mixture; and
wherein the unreacted epoxidized fatty ester is present in an amount of at least 0.5 wt-%, based on the total weight of the mixture;
wherein the epoxidized fatty ester is selected to provide a fibrous web that demonstrates greater tensile strength after aging at a temperature of 135° F. for at least 25 days in an aqueous cleaning and/or disinfecting solution, compared to a fibrous web made of fibers of the same aliphatic polyester, without the epoxidized fatty ester, to an extent of greater than 10%; and
an aqueous composition contacting the fibrous web, the aqueous composition comprising:
water; and
a surfactant and/or a biocide.

13. The wet wipe of claim 12 wherein the aqueous composition comprises a surfactant, wherein the wet wipe is a cleaning wipe.

14. The wet wipe of claim 12 wherein the aqueous composition comprises a biocide, wherein the wet wipe is a disinfecting wipe.

15. The wet wipe of claim 12 wherein the aqueous composition comprises a biocide and a surfactant, wherein the wet wipe is a cleaning/disinfecting wipe.

16. A process for improving the hydrolytic stability of a wet wipe comprising a fibrous web, wherein the fibrous web comprises fibers comprising an aliphatic polyester, the method comprising:

mixing components comprising an aliphatic polyester having a number average molecular weight of at least 8,000 Daltons, an epoxidized fatty ester, and an optional shrink reduction additive to form a mixture;

wherein the unreacted epoxidized fatty ester has at least 4.7 wt-% oxirane oxygen, based on the total weight of the epoxidized fatty ester; and wherein the unreacted epoxidized fatty ester is present in an amount of at least 0.5 wt-%, based on the total weight of the mixture;

forming fibers out of the mixture;

forming a fibrous web out of the fibers; and contacting the fibrous web with an aqueous composition comprising water and a surfactant and/or a biocide to form a wet wipe;

wherein the epoxidized fatty ester is selected to provide a fibrous web that demonstrates greater tensile strength after aging at a temperature of 135° F. for at least 25 days in an aqueous cleaning and/or disinfecting solution, compared to a fibrous web made of fibers of the same aliphatic polyester, without the epoxidized fatty ester, to an extent of greater than 10%.

* * * * *

UNITED STATES PATENT AND TRADEMARK OFFICE
CERTIFICATE OF CORRECTION

| | |
|---|---|
| PATENT NO. | : 9,982,128 B2 |
| APPLICATION NO. | : 15/024203 |
| DATED | : May 29, 2018 |
| INVENTOR(S) | : Yifan Zhang et al. |

It is certified that error appears in the above-identified patent and that said Letters Patent is hereby corrected as shown below:

On the Title Page

<u>Column 1, item (Notice)</u>
After "0 days." delete "days.".

In the Specification

<u>Column 5</u>
Line 18, Delete "then" and insert -- than --, therefor.

<u>Column 6</u>
Line 44, Delete "catemary" and insert -- catenary --, therefor.

<u>Column 6</u>
Line 48, Delete "glutartic" and insert -- glutaric --, therefor.

<u>Column 9</u>
Line 45, Delete "estification" and insert -- esterification --, therefor.

<u>Column 9</u>
Line 46, Delete "Preferrably," and insert -- Preferably, --, therefor.

<u>Column 9</u>
Line 48, Delete "epoxidization" and insert -- epoxidation --, therefor.

<u>Column 11</u>
Line 11 (approx.), Delete "poly(vinylidine" and insert -- poly(vinylidene --, therefor.

Signed and Sealed this
Second Day of April, 2019

Andrei Iancu
*Director of the United States Patent and Trademark Office*

Column 14
Line 46, Delete "zwitteronic" and insert -- zwitterionic --, therefor.

Column 14
Line 65, Delete "Dephypon" and insert -- Dehypon --, therefor.

Column 15
Lines 21-22, Delete "tricosan," and insert -- triclosan, --, therefor.

Column 15
Line 22, Delete "0-penyl-phenol," and insert -- o-phenyl-phenol, --, therefor.

Column 15
Line 42, Delete "Pseudamonas" and insert -- Pseudomonas --, therefor.

Column 17
Line 12 (approx.), Delete "poly(vinylidine" and insert -- poly(vinylidene --, therefor.

Column 19
Line 22, Delete "autogeneous" and insert -- autogenous --, therefor.

Column 19
Line 66, Delete "autogeneous" and insert -- autogenous --, therefor.

Column 20
Line 17, Delete "Mich.)" and insert -- Mich.), --, therefor.

Column 21
Line 27 (approx.), Delete "Metrom" and insert -- Metrohm --, therefor.